(12) United States Patent
Yang et al.

(10) Patent No.: US 10,918,660 B2
(45) Date of Patent: Feb. 16, 2021

(54) COMBINATION AND BALANCED NUTRITIOUS FOOD FOR IMPROVING INTESTINAL MICRO-ECOLOGY AND PREVENTING CHRONIC DISEASE, AND APPLICATION THEREOF

(71) Applicant: BEIJING RUIQIANJING SCIENCE AND TECHNOLOGY DEVELOPMENT CO. LTD., Beijing (CN)

(72) Inventors: Bingjun Yang, Beijing (CN); Mingguo Chi, Beijing (CN); Jing Yuan, Beijing (CN); Wei Bi, Beijing (CN); Weiwei Cheng, Beijing (CN)

(73) Assignee: BEIJING RUIQIAN SCIENCE AND TECHNOLOGY DEVELOPMENT CO. LTD., Beijing (CN)

( * ) Notice: Subject to any disclaimer, the term of this patent is extended or adjusted under 35 U.S.C. 154(b) by 0 days.

(21) Appl. No.: 16/615,820

(22) PCT Filed: Oct. 23, 2017

(86) PCT No.: PCT/CN2017/107252
§ 371 (c)(1),
(2) Date: Nov. 22, 2019

(87) PCT Pub. No.: WO2018/214395
PCT Pub. Date: Nov. 29, 2018

(65) Prior Publication Data
US 2020/0078391 A1 Mar. 12, 2020

(30) Foreign Application Priority Data
May 23, 2017 (CN) .......................... 2017 1 0367848

(51) Int. Cl.
| | | |
|---|---|---|
| A61K 31/733 | (2006.01) |
| A23L 33/24 | (2016.01) |
| A23L 33/26 | (2016.01) |
| A23L 7/10 | (2016.01) |
| A23L 29/244 | (2016.01) |
| A61P 9/00 | (2006.01) |
| A61P 3/10 | (2006.01) |
| A61P 1/00 | (2006.01) |
| A61K 31/702 | (2006.01) |
| A61K 31/717 | (2006.01) |
| A61P 19/06 | (2006.01) |
| A61P 29/00 | (2006.01) |
| A61P 3/00 | (2006.01) |
| A23L 33/125 | (2016.01) |
| A23L 7/143 | (2016.01) |
| A23L 7/109 | (2016.01) |
| A21D 2/36 | (2006.01) |
| A21D 13/062 | (2017.01) |
| A61K 31/716 | (2006.01) |
| A23L 33/21 | (2016.01) |

| | |
|---|---|
| A61P 3/06 | (2006.01) |
| A23P 30/20 | (2016.01) |

(52) U.S. Cl.
CPC .............. *A61K 31/733* (2013.01); *A21D 2/36* (2013.01); *A21D 13/062* (2013.01); *A23L 7/10* (2016.08); *A23L 7/109* (2016.08); *A23L 7/143* (2016.08); *A23L 7/198* (2016.08); *A23L 29/244* (2016.08); *A23L 33/125* (2016.08); *A23L 33/21* (2016.08); *A23L 33/24* (2016.08); *A23L 33/26* (2016.08); *A61K 31/702* (2013.01); *A61K 31/716* (2013.01); *A61K 31/717* (2013.01); *A61P 1/00* (2018.01); *A61P 3/00* (2018.01); *A61P 3/06* (2018.01); *A61P 3/10* (2018.01); *A61P 9/00* (2018.01); *A61P 19/06* (2018.01); *A61P 29/00* (2018.01); *A23P 30/20* (2016.08); *A23V 2002/00* (2013.01)

(58) Field of Classification Search
None
See application file for complete search history.

(56) References Cited

FOREIGN PATENT DOCUMENTS

| | | |
|---|---|---|
| CN | 101268830 A | 9/2008 |
| CN | 101537020 A | 9/2009 |
| CN | 101766226 A | 7/2010 |

(Continued)

OTHER PUBLICATIONS

CN101537020B, published Sep. 23, 2009, machine translation. (Year: 2009).*

(Continued)

*Primary Examiner* — Layla D Berry
(74) *Attorney, Agent, or Firm* — Bayramiogiu Law Offices LLC (57) ABSTRACT

A combination for improving intestinal micro-ecology and preventing chronic diseases includes an inulin, a galactooligosaccharide and a dietary fiber composite, wherein the ratio of the inulin, the galactooligosaccharide and the dietary fiber composite in a formula is (1-75):(1-75):(5-95). Preferably, the ratio is (10-50):(10-50):(25-50). A balanced nutritious food includes cereal flour and the ratio of the cereal flour to the combination in a formula is (50-95):(5-50). Preferably, the ratio is (70-95):(30-5). Moreover, provided is an application in preparing foods or medicaments for preventing inflammatory bowel disease, improving gastrointestinal motility and preventing constipation, preventing diabetes, preventing cardiovascular and cerebrovascular diseases, and regulating intestinal flora to enhance immune ability.

17 Claims, 5 Drawing Sheets

(56) References Cited

FOREIGN PATENT DOCUMENTS

| | | |
|---|---|---|
| CN | 102511713 A | 6/2012 |
| CN | 102511714 A | 6/2012 |
| CN | 103168993 A | 6/2013 |
| CN | 103750104 A | 4/2014 |
| CN | 104171803 A | 12/2014 |
| CN | 104366649 A | 2/2015 |
| CN | 104473292 A | 4/2015 |
| CN | 104543848 A | 4/2015 |
| CN | 105146369 A | 12/2015 |
| CN | 107198250 A | 9/2017 |

OTHER PUBLICATIONS

CN106360310A, published Feb. 1, 2017, machine translation. (Year: 2017).*

* cited by examiner

COMBINATION AND BALANCED NUTRITIOUS FOOD FOR IMPROVING INTESTINAL MICRO-ECOLOGY AND PREVENTING CHRONIC DISEASE, AND APPLICATION THEREOF

CROSS REFERENCE TO THE RELATED APPLICATIONS

This application is the national phase entry of International Application No. PCT/CN2017/107252, filed on Oct. 23, 2017, which is based upon and claims priority to Chinese Patent Application No. 2017103678481, filed on May 23, 2017, the entire contents of which are incorporated herein by reference.

TECHNICAL FIELD

The present disclosure relates to the fields of disease prevention and nutritious foods targeting intestinal microorganisms. More specifically, the present disclosure relates to a combination and a balanced nutritious food for improving intestinal micro-ecology and preventing a chronic disease, and an application thereof.

BACKGROUND

The human body is a "super-organism" composed of human cells and all commensal microorganisms and the human body is also an extremely complex ecosystem. The number of microbial cells living inside and outside the human body is 10 times the number of the human cells and even up to more than one hundred trillion. More than 90% of the commensal microorganisms live in the human body and are known as "human gastrointestinal microbiota". Bacteria inhabit in an adult intestinal tract in an order of magnitude of approximately $10^{14}$, which is mainly colonized in the colon and forms a microbial ecosystem having the weight of about 1.5 kg where 1,000-1,150 species of bacteria are included. Since the twenty first century, mankind has faced the enormous challenge of "Dietary Fiber Gap". "Dietary Fiber Gap" refers to the difficultly of people eating enough dietary fiber according to recommended standards. When not enough dietary fiber is consumed by an individual, some of the intestinal microorganisms disappear, human gastrointestinal microbiota is destroyed, the intestinal permeability is increased, the human body has a chronic low-grade inflammatory state, has a lower immunity, and thereby causing various chronic diseases.

Currently, there is a viewpoint that numerous health issues in the human body are caused by microbiota imbalance inside the body and the determining factor is the micro-ecology balance. For example, intestinal flora is associated with obesity and the mechanism of the obesity caused by intestinal flora imbalance is mainly as follows. Some butyric acid-producing bacteria can degrade the glycans in the diet and convert them into short-chain fatty acids for absorption and utilization by the body, resulting in an increase in the host's ability to absorb energy from the diet. The intestinal flora can further regulate the expression activity of genes in tissues for energy storage and the genes mainly related to lipogenesis are fasting-induced adipose factor (Fiaf) and carbohydrate response element-binding protein (ChREBP)/sterol regulatory element-binding protein 1 (SREBP-1). High-fat diets cause metabolic endotoxemia by altering the structure of the intestinal flora, and then induce chronic systemic inflammation through the lipopolysaccharide (LPS)/cluster of differentiation 14 (CD14) signal pathway, causing obesity and insulin resistance.

Research further shows that the metabolites of the intestinal flora are associated with the increased incidence of major cardiovascular adverse events and the intestinal flora is associated with colorectal cancer. Moreover, there is another viewpoint that the toxin produced by the intestinal flora is an important cause of aging and illness.

Based on new understanding of intestinal flora, intestinal flora is an important factor in causing multiple chronic diseases and treatment of diseases. Intestinal flora has plasticity and therefore is an ideal novel target for the prevention and treatment of diseases. So far, research has found that regulating the balance of intestinal micro-ecology can achieve the purpose of relieving and treating diseases. For example, domestic and foreign research has confirmed that specific clinically proven probiotics can be used to effectively treat syndromes such as diarrhea, constipation and vaginal infections. It has also been reported that the regulation of the structure of the intestinal flora by oligofructose prebiotics can affect the synthesis and secretion of various gastrointestinal hormones. For instance, increasing the concentrations of glucagon-like peptide-1 (GLP-1) and glucagon-like peptide-2 (GLP-2) and decreasing the concentration of dipeptidyl peptidase IV (DPP-4) in the colon, metabolic endotoxemia is thereby improved. In another example, alpha glycosidase inhibitors can significantly increase the number of probiotics such as bifidobacteria, improve glucose metabolism, and reduce adipose tissue inflammation. Research further shows that dietary fiber can slow down the digestion rate, accelerate the excretion of cholesterol, and reduce the risk of intestinal cancer. Meanwhile, dietary fiber can absorb toxic substances in food, prevent obesity, intestinal diseases, cardiovascular diseases and diabetes, decrease blood pressure, prevent breast cancer, change the compositions of microbial community in the intestinal system to balance the microbiota, and improves the body's immune function.

However, numerous drawbacks still exist in the existing research and in applications. The enormous challenge of "Dietary Fiber Gap" faced by humans since the twenty first century has not been solved, which causes some intestinal microorganisms to disappear and the intestinal flora to be destroyed, thereby causing various chronic diseases. These chronic diseases, as causes, account for 85% of human deaths and are still increasing. There is no effective and sufficient nutritional combination to improve the imbalance of the intestinal flora. A single addition of the edible functional glycan combination or the common glycan combination has a positive effect on the human body, but it will also cause a negative effect such as excess or insufficiency of individual beneficial bacteria, and increased intestinal permeability in stages. There is lack of research and applications of synergistic effect between the combination of major functional glycan prebiotics and the common glycans composited celluloses to overcome the drawbacks and shortcomings of the simple glycans combinations. There is a lack of staple foods that satisfies both the human body and intestinal flora (the super-organism), so that primary prevention cannot be performed conveniently to fundamentally ensure human health.

In summary, in recent years, techniques such as microbiology, metabolomics, proteomics, transcriptomics, and metagenomic association analysis have been gradually applied to the study of intestinal microorganisms, which has a great promotion for the interpretation of the relationship between intestinal bacteria and human health, and research on the role of intestinal bacteria in the occurrence of diseases. Crucial nutritional health problems include developing a combination that improves the intestinal micro-ecology, eliminating pathogenic factors such as chronic inflammation and low immunity, improving the body in a sub-health state, preventing chronic diseases such as cardiovascular and cerebrovascular diseases, diabetes, chronic neurodegenerative diseases and cancer, and developing foods that satisfy both the human body and the intestinal micro-ecology. Namely, developing a staple food for the super-organism and solving the "Dietary Fiber Gap". In this regard, the present invention develops a novel combination and a balanced nutritious food for maintaining intestinal micro-ecology and providing nutrition to microbiota, which improves the human body in the sub-health state, effectively prevents non-infectious chronic diseases in primary prevention, and is currently one of the most important research and development topics.

SUMMARY

The technical problem to be solved by the present invention is to provide a combination for improving intestinal micro-ecology and preventing chronic diseases. The combination can promote the growth and reproduction of probiotics, maintain the survival of appropriate amount of non-probiotic bacteria, inhibit the growth and activity of harmful bacteria, maintain the balance of intestinal microbial homeostasis, reduce intestinal permeability, blood endotoxin and inflammatory factors, enhance cell metabolism and body immunity, metabolize nutrients such as short-chain fatty acids, branched-chain amino acids and vitamins, reduce pH in the intestine, promote the absorption of minerals such as calcium, ferrum and magnesium, eliminate pathogenic factors including chronic inflammation and low immunity, improve the body in a sub-health state, and prevent chronic diseases such as cardiovascular and cerebrovascular diseases and diabetes in primary prevention.

In order to solve the above technical problem, the present invention provides a combination for improving intestinal micro-ecology and preventing chronic diseases, including an inulin, a galactooligosaccharide and a dietary fiber composite, wherein a ratio of the inulin, the galactooligosaccharide and the dietary fiber composite in a formula is (1-75):(1-75):(5-95) by weight.

As an improvement of the present invention, the ratio of the inulin, the galactooligosaccharide and the dietary fiber composite in the formula is (10-50):(10-50):(25-50) by weight.

Further, the inulin is oligofructose, polyfructose, or the mixture of the oligofructose and the polyfructose; the dietary fiber composite is a mixture of a soluble non-prebiotic fiber and an insoluble non-prebiotic fiber, wherein a ratio of the soluble non-prebiotic fiber to the insoluble non-prebiotic fiber is (10-90):(10-90). The ratio of a functional glycan inulin, the galactooligosaccharide and common glycan dietary fiber composite in the formula is 25:25:50, 25:50:25 or 35:15:50.

Further, the soluble non-prebiotic fiber is a resistant dextrin, a polydextrose, an oligo-isomaltose or the mixture thereof. The insoluble fiber is a water-insoluble cellulose, a hemicellulose, a lignin or the mixture thereof.

The present invention further provides a balanced nutritious food including the above combination. The balanced nutraceutical food further includes a cereal flour, a ratio of the cereal flour to the combination in a formula is (50-95):(50-5).

Further, the ratio of the cereal flour to the combination in the formula is (70-95):(30-5).

Further, the cereal flour is one or more selected from the group consisting of wheat flour, rice flour, corn flour and whole potato powder. The balanced nutritious food is prepared in a form of compound rice, flour, noodles, pasta, rice noodles, bread, bread dough or bread mix.

Further, a method for preparing the compound rice includes mixing the cereal flour with the combination and extruding into a shape of rice by an extruding process, wherein the insoluble cellulose in the combination is microcrystalline cellulose.

The present invention further discloses an application of the above combination in a preparation of a food or a medicament for preventing inflammatory bowel disease.

The present invention further discloses an application of the above combination in a preparation of a food or a medicament for improving gastrointestinal motility and preventing constipation.

The present invention further discloses an application of the above combination in a preparation of a food or a medicament for preventing diabetes.

The present invention further discloses an application of the above combination in a preparation of a food or a medicament for preventing cardiovascular and cerebrovascular diseases.

The present invention further discloses an application of the above combination in a preparation of a food or a medicament for regulating intestinal flora and enhancing the immune system.

For such a design, the present invention has at least the following advantages.

The combination of the present invention includes a combination of functional glycan prebiotics, which provides food for intestinal probiotics, promotes the growth and reproduction of beneficial bacteria, inhibits the growth and activity of harmful bacteria, and maintains the steady state balance of intestinal microorganisms. Moreover, the common glycan dietary fiber composite included therein has the functions of fermentability, water swelling, gradient adhesion, mechanical isolation, mesh adsorption, ion exchange and bacterial flora regulation, which provides a favorable environment for the growth of beneficial bacteria in the intestinal, slows down the digestion rate, accelerates the excretion of cholesterol, absorbs toxic substances in food, and maintains the survival of appropriate amount of non-probiotic bacteria. The synergistic action of functional glycans and common glycans eliminates the negative effects of the functional glycans or the common glycans alone, reduces intestinal permeability, blood endotoxin and inflammatory factors, enhances cell metabolism and body immunity, metabolize nutrients such as short-chain fatty acids, branched-chain amino acids and vitamins, reduces pH in the intestinal, promotes the absorption of minerals such as calcium, ferrum and magnesium, eliminates pathogenic factors including chronic inflammation and low immunity, improves the body in a sub-health state, and prevents chronic diseases such as cardiovascular and cerebrovascular diseases and diabetes in primary prevention. The combination of the present invention can well maintain the steady state environment of intestinal microorganisms and prevent chronic diseases.

In the present invention, the balanced nutritious food including the above combination is a staple food that is indispensable for people every day, not only providing nutrients for the human body itself, but also providing environment and nutrients for the flora symbiotic with the human body, which maintains the balanced nutrition of the human body which is regarded as a super-organism, effectively improves the human body in a sub-health state, prevents diseases and protects health.

BRIEF DESCRIPTION OF THE DRAWINGS

The above is only a summary of the technical solutions of the present invention. For a clear understanding of the technical means of the present invention, the present invention is further described in detail below with reference to the accompanying drawings and specific embodiments.

DETAILED DESCRIPTION OF THE EMBODIMENTS

In the present invention, a combination for improving intestinal micro-ecology and preventing chronic diseases includes an inulin, a galactooligosaccharide and a dietary fiber composite, wherein the ratio of the inulin, the galactooligosaccharide and the dietary fiber composite in a formula is (1-75):(1-75):(5-95) by weight.

In the present invention, the inulin is oligofructose, polyfructose, or the mixture of the oligofructose and the polyfructose. Galactooligosaccharides (GOS) are functional oligosaccharides with natural properties, and the molecular structure thereof is generally formed by linking 1-7 galactosyl groups to a galactose (Gal) or glucose (Glc) molecule, namely Gal-(Gal)n-Glc/Gal (n is 0-6). The dietary fiber composite is the mixture of a soluble non-prebiotic fiber and an insoluble non-prebiotic fiber, wherein the soluble non-prebiotic fiber is a resistant dextrin, a polydextrose, an oligo-isomaltose or the mixture thereof. The insoluble fiber (solkfloc) is a water-insoluble cellulose, a hemicellulose, a lignin or the mixture thereof. In this embodiment, the ratio of the soluble non-prebiotic fiber to the insoluble non-prebiotic fiber is (10-90):(10-90).

In the present invention, a preferred ratio of the inulin, the galactooligosaccharide and the dietary fiber composite in the formula is (10-50):(10-50):(25-50).

In the present invention, a more preferred ratio of the inulin, the galactooligosaccharide and the dietary fiber composite in the formula is 25:25:50, 25:50:25 or 35:15:50.

In order to make the combination for improving intestinal micro-ecology better in acting on the human body, the present invention further provides a balanced nutritious food including the above combination. The balanced nutraceutical food includes a cereal flour and the above combination, the ratio of the cereal flour to the combination in a formula is (50-95):(50-5).

The cereal flour is wheat flour, rice (japonica rice, indica rice, glutinous rice) flour, corn flour, whole potato powder or the combination thereof. The balanced nutritious food formed by the cereal flour and the above combination mainly includes various forms of food such as compound rice, flour, noodles (hand-made noodles, dried noodles, semi-dried noodles, wet noodles), pasta, rice noodles, bread, bread dough, bread mix or equivalent or similar food forms, but are not limited to the above forms.

In the present invention, a preferred ratio of the cereal flour to the combination in the formula is: (70-95):(30-5).

In the present invention, a more preferred ratio of the cereal flour to the combination in the formula is: 70:30, 85:15 or 88:12.

Obviously, the balanced nutritious food of the present invention may further include minerals, vitamins, and nutritional enhancers and supplements such as xylooligosaccharide, L-arabinose, stachyose, guar gum or equivalent supplements, and the scope of their additions are in accordance with the requirements of General Principles for the Addition of Essential Nutrients to Foods established by the Codex Alimentarius Commission (CAC).

In the present invention, the functional glycan inulin, galactooligosaccharide and stachyose are all prebiotics, and can inhibit the growth and activity of harmful bacteria by selectively stimulating the growth and activity of one or several kinds of beneficial bacteria. This prebiotic combination provides "food" for the probiotics in the intestinal, promotes the growth and reproduction of beneficial bacteria, and inhibits the growth and activity of harmful bacteria. The common glycan combination in the combination of the present invention maintains the survival of appropriate amount of non-probiotic bacteria. The insoluble dietary fiber composite has the functions of fermentability, water swelling, gradient adhesion, mechanical isolation, mesh adsorption, ion exchange and flora regulation, which provides a favorable environment for the growth of beneficial bacteria in the intestinal, slows down the digestion rate, accelerates the excretion of cholesterol, absorbs the toxic substances in food, and reduces the risk of colorectal cancer. Therefore, the balanced nutritious food of the present invention can well maintain a steady state environment of intestinal microorganisms, reduce intestinal permeability, prevent chronic diseases in primary prevention, and protect human health.

Embodiment 1 of Product: Balanced Nutritious Rice

The cereal flour is a rice flour mixture formed by mixing japonica rice flour with glutinous rice flour in the ratio of 80:20 by weight. The flora nutrition combination is the mixture including an inulin, a galactooligosaccharide, a polydextrose, and a microcrystalline cellulose in the ratio of 30:20:25:25 by weight, and the ratio of the cereal flour to the flora nutrition combination is 85:15 by weight.

A method for preparing the balanced nutritious rice is as follows.

1. The components of the flora nutrition combination are taken according to the ratio and mixed thoroughly with a blender to prepare a premixed powder material for subsequent use.

2. The japonica rice flour is mixed with the glutinous rice flour in a ratio of 80:20 to obtain the rice flour mixture. The rice flour mixture is mixed with the premixed powder material obtained in the step 1 in the ratio of 80:20 by weight. Then, stirring is performed by adding 27%-29% water by weight to obtain a semi-finished product of the balanced nutritious rice.

3. The semi-finished product of the balanced nutrient rice obtained in the step 2 is extruded and granulated by a twin-screw extruder, then dried by a fluidized bed dryer, and subsequently cooled and sieved to obtain the balanced nutritious rice of this embodiment.

In this embodiment, the finished product of the balanced nutritious rice has a similar shape of natural rice with an attractive appearance. The taste is delicate and smooth without any granule feeling or retrogradation. Moreover, it meets the balanced nutritional requirements of the super organism (composed of human body and intestinal flora), has a glycemic indicator less than 50, and can improve constipation, proliferate probiotics, reduce pH in the intestinal and improve the intestinal micro-ecological environment.

Embodiment 2 of Product: Balanced Nutritious Flour

The cereal flour is a common flour, and the flora nutrition combination is the mixture formed by mixing an inulin, a galactooligosaccharide, a polydextrose and a microcrystalline cellulose in the ratio of 25:25:20:30 by weight, and the ratio of the cereal flour to the flora nutrition combination is 90:10 by weight.

A method for preparing the balanced nutritious flour is as follows.

1. The components of the flora nutrition combination are taken according to the ratio and mixed thoroughly with a blender to prepare a premixed powder material for subsequent use.

2. The common flour is mixed with the premixed powder material obtained in the step 1 in the ratio of 90:10 by weight, followed by stirring sufficiently and sieving to obtain the balanced nutritious flour of this embodiment.

In this embodiment, the finished product of the balanced nutritious flour has a similar shape of the common flour with a delicate taste and without a granule feeling when making various kinds of wheaten foods. It meets the balanced nutritional requirements of the super organism (composed of human body and intestinal flora), enhances water absorption, has a glycemic indicator less than 50, and can proliferate probiotics, reduce pH in the intestinal and improve constipation and the intestinal micro-ecological environment.

Embodiment 3 of Product: Balanced Nutritious Noodles

The cereal flour is a common flour, and the flora nutrition combination is the mixture formed by mixing an inulin, a galactooligosaccharide, a polydextrose and a microcrystalline cellulose in the ratio of 25:25:25:25 by weight, and the ratio of the cereal flour to the flora nutrition combination is 70:30 by weight.

A method for preparing the balanced nutritious noodles is as follows.

1. The components of the flora nutrition combination are taken according to the ratio and mixed thoroughly with a blender to prepare a premixed powder material for subsequent use.

2. The common flour is mixed with the premixed powder material obtained in the step 1 in the ratio of 70:30 by weight and then stirred by adding water to a water content of about 50% with an appropriate water temperature of 15-20° C. for 10-15 minutes.

3. Ripening is performed for 10-15 minutes at a ripening temperature of about 25° C., followed by rolling, cutting, drying, shaping in cold air, and reducing the water content to 14% to obtain the balanced nutritious noodles of this embodiment.

In this embodiment, the balanced nutritious noodles have a delicate, smooth and chewy taste. They meet the balanced nutritional requirements of the super organism (composed of human body and intestinal flora), have a glycemic indicator less than 50, and can proliferate probiotics, reduce pH in the intestinal and improve constipation and the intestinal micro-ecological environment.

Embodiment 4 of Product: Balanced Nutritious Bread

The cereal flour is a medium-gluten flour, and the flora nutrition combination is the mixture formed by mixing an inulin, a galactooligosaccharide, a polydextrose and a microcrystalline cellulose in the ratio of 25:20:25:30 by weight, and the ratio of the cereal flour to the flora nutrition combination is 88:12 by weight.

A method for preparing the balanced nutritious bread is as follows.

1. The components of the flora nutrition combination are taken according to the ratio and mixed thoroughly with a blender to prepare a premixed powder material for subsequent use.

2. The medium-gluten flour is mixed with the premixed powder material obtained in the step 1 in the ratio of 85:15 by weight and then stirred by adding water. The balanced nutritious bread loaf of this embodiment is obtained by dough kneading, a first fermentation, a second dough mixing treatment, a second fermentation, shaping, molding, pre-baking processing, baking, and cooling according to the traditional bread process. In this step, the ingredients, such as white sugar, vegetable oil and other ingredients, required in the traditional method for making bread, are eliminated thanks to the characteristics of the components of the flora nutrition combination.

In this embodiment, the balanced nutritious bread has a delicate and smooth taste, a fluffy and soft structure, and a resistance against collapse. It meets the balanced nutritional requirements of the super organism (composed of human body and intestinal flora), has a glycemic indicator less than 50, and can proliferate probiotics, reduce pH in the intestinal and improve constipation and the intestinal micro-ecological environment.

The combination for improving intestinal micro-ecology of the present invention includes functional glycans and common glycan dietary fibers. A plurality of the glycans have a remarkable synergistic effect, which generates positive effects on the host without negative effects. A combined nutrient and an intestinal environment that is beneficial to the proliferation are provided for beneficial bacteria and neutral bacteria in the intestine, which enriches the metabolites of intestinal flora including primary metabolites and secondary metabolites beneficial to the human body, improves the intestinal micro-ecology, and achieves the effect of preventing chronic diseases targeted by improving intestinal microbial steady state. The balanced nutritious food of the present invention further provides a balanced nutrition for the intestinal flora and the human body (super organism), and provides a combination for maintaining the steady state balance of the intestinal micro-ecology with its suitable staple food as a carrier, which effectively improves the human body in a sub-health state, and prevents chronic diseases that cause major human health problems.

Embodiment of Application

In this experiment, glycan combinations are divided into three types including 1) a combination of functional glycans; 2) a combination of common glycans; 3) a combination including a plurality of functional glycans and common glycans, which are used to determine a synergistic effect of different types of the glycan combinations. The synergistic effect mainly includes the following two aspects. First, changes of suitable microbial abundance and the microbial living environment. Second, changes of the effects on the physiological indicator of the host. The specific steps of the experiment are as follows.

1. Materials and Devices 1.1 Reagents

DAO kit, SCFA kit, TMAO kit, provided by Shanghai Meilian Biotechnology Co., Ltd.

1.2 Experimental Animals 8-week-old specific pathogen-free (SPF) grade BARBL/C mice, purchased from the Experimental Animal Center of the Academy of Military Medical Sciences.

1.3 Experimental Feed

Four experimental feed groups were prepared according to the classification of the above glycan combinations.

Blank group O: 100% base feed. Namely, the common feed for mice.

Experimental group A: base feed+combination of functional glycans. Specifically, 85% base feed, 7.5% galactooligosaccharide, and 7.5% inulin.

Experimental group B: base feed+combination of common glycans. Specifically, 85% base feed, 7.5% insoluble dietary fiber (wheat bran extract), and 7.5% polydextrose.

Experimental group C: base feed+combination of functional glycans+combination of common glycans. Specifically, 85% base feed, 4% galactooligosaccharide, 3.5% inulin, 4% insoluble dietary fiber, and 3.5% polydextrose.

The above experimental feeds were all provided by Beijing Ruiqianjing Science and Technology Development Co., Ltd. Moreover, since the above formulas are to be made into food, the effect to be reached refers to 37-45 g of edible dietary fiber composite for 250-300 g of staple food per day.

1.4 Main Instruments and Devices

An electronic balance and a pH meter, provided by Mettler-Toledo Instruments (Shanghai) Co., Ltd; a gas chromatography mass spectrometer (GC-MS).

2. Experimental Methods 2.1 Experimental Design

The mice were randomly allocated into the blank group O, the experimental group A, the experimental group B, and the experimental group C (8 mice/group) and were fed in an individually ventilated caging system where 12 h light/12 h night was strictly controlled and the ambient temperature was set to be 22° C.

The experiment lasted 4 weeks, wherein the first week was the adaptation period, and the second, third and fourth weeks were the experimental period. During the adaptation period, all four groups of mice were fed with the blank feed (i.e. 100% base feed). During the experimental period, the mice of the blank group O were fed with the blank feed, and the mice of the experimental groups were fed with the corresponding feeds in the experimental group A, experimental group B, and experimental group C, respectively. At the end of the second week and the end of the third week during the experimental period, 3 mice were randomly selected, blood was collected from the eyeball, the mice were sacrificed by dislocation, the small intestine was taken and stored in a formalin solution for hematoxylin-eosin (HE) staining. The colon content samples were collected and stored at −80° C. and the pH, bacterial flora composition and the like were analyzed. Serum was separated after collecting the blood. Various biochemical indicators such as diamine oxidase (DAO), trimethylamine oxide (TMAO) and short-chain fatty acid (SCFA) in the serum were measured by the kits.

2.2 Determination of Serum Metabolic Parameters

After the blood was taken from the mouse eyeballs, the blood was placed at room temperature for 1 h, and centrifuged at 3000 rpm for 15 min for separation to obtain a supernatant serum, and the supernatant serum was stored at −80° C. The biochemical indicators of the serum, including DAO, TMAO and SCFA, were determined by the kits.

2.3 Determination of pH of Intestinal Contents 100 mg of the intestinal contents was weighed, added with deionized water at 15 mL/g, sufficiently dispersed, and centrifuged at 13,000 g for 2 min, and then the pH of the supernatant was measured with a pH meter.

2.4 Determination of Metabolomics of Intestinal Contents 100 mg of the sample was weighed, added with a solution formed by methanol, water and chloroform in a ratio of 3:1:1, uniformly dispersed by vortex shaking, placed for 12 h, and centrifuged to obtain a supernatant. 100 μl of the extract was taken, added with 20 μL of 0.2 mg/mL ribitol as an internal standard substance, sufficiently mixed, and then dried by blowing $N_2$ at 45° C. 40 μL of 20 mg/mL methoxyamine hydrochloride solution was added to the dried extract, sufficiently mixed, and reacted at 130 rpm for 90 min at 30° C. After sufficient reaction, 40 μL of N, O-bis (trimethylsilyl) trifluoroacetamide (BSTFA) (containing 1% trimethylchlorosilane (TMCS)) was further added, sufficiently mixed, then maintained in a gas bath at 37° C. for 30 min, followed by taking out and placed at room temperature for 120 min, and then stored at 4° C. for subsequent determination.

GC-MS Chromatographic Conditions:

Gas chromatography (GC) conditions: Agilent 7890, tandem LECO Pegasus 4D TOF/MS instrument;

Gerstel multipurpose sampler (MPS) injection system;

Column: DB-5MS 30 m×250 μm×0.25 mm;

Temperature programming: 70° C., kept for 1 min, raised to 280° C. at 5° C./min, kept for 10 min;

Carrier gas was He; flow rate was 1 mL/min; injection volume was 1 μL; and split ratio was 1:2.

Mass spectrometry (MS) conditions:

MS conditions: electron ionization (EI) source: mass scanning range of 50-800 Da, scanning speed of 10/s; temperatures at injection port, transmission line and ion source were 250° C., 250° C. and 220° C., respectively.

Data Processing

Each compound in the chromatogram was subjected to chromatographic peak alignment, deconvolution, and peak search by the workstation Chroma TOF software 4.50 version (identified by mass spectrometry databases such as its own National Institute of Standards and Technology (NIST) mass spectrometry database, and related standard substance). Then, the original chromatogram was normalized by ribitol (internal standard substance) and integrated (signal-to-noise ratio S/N>100) to finally obtain related data of each chromatographic peak, metabolite name and peak area.

2.5 Measurement of Changes in Small Intestinal Villus Height and Fossae Depth

Method for analyzing villus length, fossae depth and goblet cells in the intestinal tissue by Image pro-plus 6.0 (IPP). The villus length and the fossae depth of each slice were measured by using a line tool of the IPP software to select a picture having stretched villi and having complete intestine villi.

2.6 Determination of 16S DNA of Intestinal Contents

The extraction of microbial DNA was performed according to the instructions of the kit (Omega Bio-tek, Norcross, Ga., U.S.) for extracting the DNA of the intestinal contents. The mass of the extracted DNA was detected by 1% agarose gel electrophoresis. The DNA samples were stored in a −20° C. refrigerator. The polymerase chain reaction (PCR) amplification was performed for the 16S v3-v4 hypervariable regions of the bacterial 16S rRNA gene by high-throughput sequencing in the Illumina MiSeq sequencing platform PE300 (the amplification conditions: unwinding at 95° C. for 2 min, 95° C. for 30 s, 55° C. for 30 s, 7° C. for 30 s, 25 cycles, and then extending at 72° C. for 10 min). The primers used includes the forward primer (515F) 5'-barcode-GTGCCAGCMGCCGCGG-3', and the reverse primer (907R) 5'-CCGTCAATTCMTTTRAGTTT-3', and for each sample, an 8 bp tag sequence was added. Each sample was amplified in triplicate in a 25 μL reaction system including 2.5 μL of 10× Pyrobest Buffer, 2 μL of 2.5 mM of dNTPs, 1 μL of the forward (10 μM), 1 μL of the reverse primers (10 μM), 0.4 U of a DNA polymerase. (Pyrobest DNA Polymerase, TaKaRa), 15 ng of the DNA template, and the remaining being ddH$_2$O. The amplicons were recovered by a 2% agarose gel, purified according to the instructions of the AxyPrep DNA Gel Extraction Kit (Axygen Biosciences, Union City, Calif., U.S.), and quantified by QuantiFluor™-ST (Promega, U.S.). The purified amplicons were mixed in equal amounts and were then subjected to double-ended 2×300 bp sequencing according to the standard protocol of the Illumina MiSeq sequencing platform. The original fastq file was processed by the QIIME (version 1.17) software according to the following processing criteria: (i) 10 bp was used as a sliding window. If the average mass value in the window is less than 20, then the back-end base is truncated from the window and the sequence of less than 50 bp is filtered out. (ii) The samples are distinguished according to the tag sequence. The mismatch number in the tag sequence was allowed to be 0. The mismatch number of the primers was allowed to be 2 and sequences containing the fuzzy bases were removed. (iii) Between the sequences spliced together, the overlap region should be equal to or more than 10 bp, and sequences that cannot be spliced were removed. UPARSE (version 7.1 http://drive5.com/uparse/) software was used to generate operational units (OTUs) with a similarity of 97% by clustering. Subsequently, the chimeric sequences were identified by UCHIME software and were removed. For taxonomic alignment, the Silva (SSU115) 16S rRNA database was used with an algorithm RDP Classifier (http://rdp.cme.msu.edu/) and a confidence threshold of 70%.

3. Results and Conclusions 3.1 pH of Intestinal Contents

Figure 1:
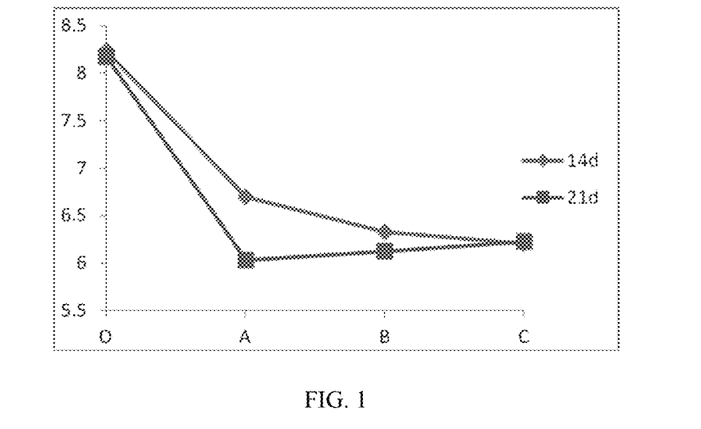
FIG. 1 is a diagram showing changes in pH of mouse intestinal contents in an embodiment of the present invention.

Referring to FIG. 1, in the mice of the blank group O, the pH values of the intestinal contents reached 8.23 and 8.17 at 14 days and 21 days, respectively. However, the pH values of the intestinal contents of the mice in the experimental groups A, B and C dropped sharply to about 6.0, and the values in the experimental group C were the most stable. This is because bacteria decompose oligosaccharides and produce short-chain fatty acids, which lowers the pH values.

The intestinal pH value is an important parameter of the intestinal micro-ecology, and the pH values change significantly. From this experiment, it can be seen that the formula feed of the experimental group C is the most stable and ideal.

3.2 Serum Biochemical Indicators of Mice

TABLE 1

Changes in serum biochemical indicators of mice after feed intervention in the experimental groups

| Treatment | Indicators | | |
|---|---|---|---|
| | SCFA(pg/ml) | TMAO(ng/ml) | DAO(U/L) |
| O-14 | 197.29 | 49.64 | 89.87 |
| A-14 | 189.75 | 62.77 | 58.33 |
| B-14 | 154.50 | 45.00 | 81.00 |
| C-14 | 145.88 | 38.38 | 76.93 |
| O-21 | 199.38 | 54.15 | 87.60 |
| A-21 | 225.62 | 79.92 | 100.67 |
| B-21 | 233.75 | 102.08 | 91.40 |
| C-21 | 196.13 | 51.31 | 70.87 |

Figure 2:
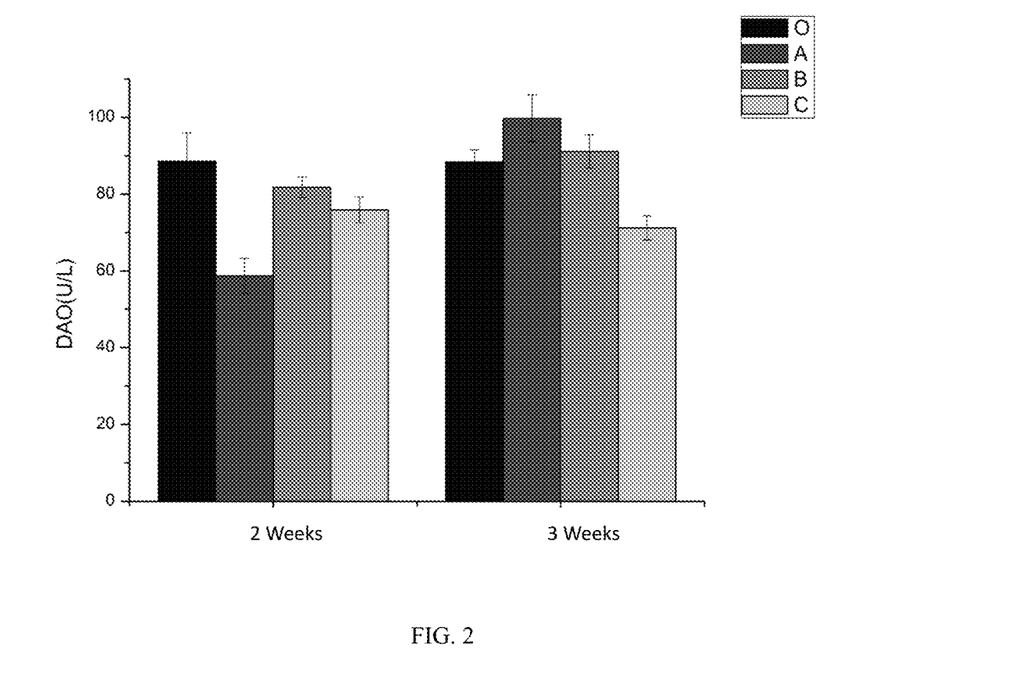
FIG. 2 is a diagram showing changes in the biochemical indicator of diamine oxidase (DAO) of mouse serum in an embodiment of the present invention.
Figure 3:
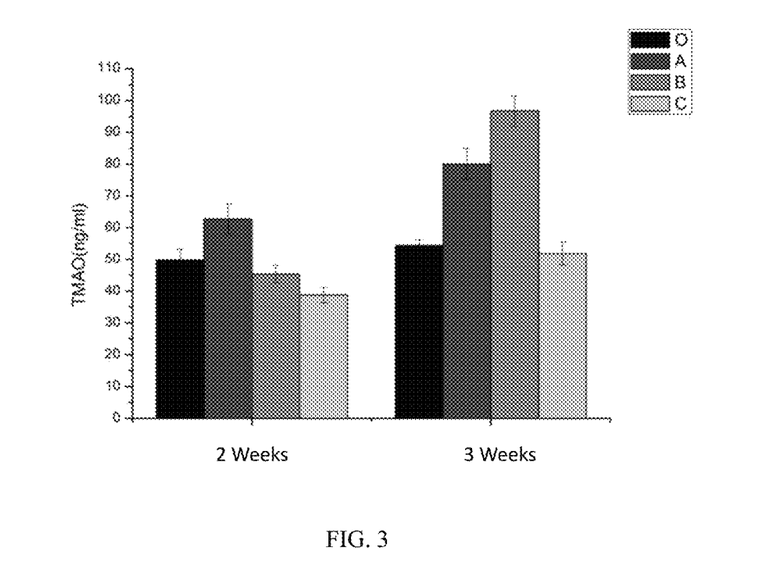
FIG. 3 is a diagram showing changes in the biochemical indicator of trimethylamine N-oxide (TMAO) of mouse serum in an embodiment of the present invention.
Figure 4:
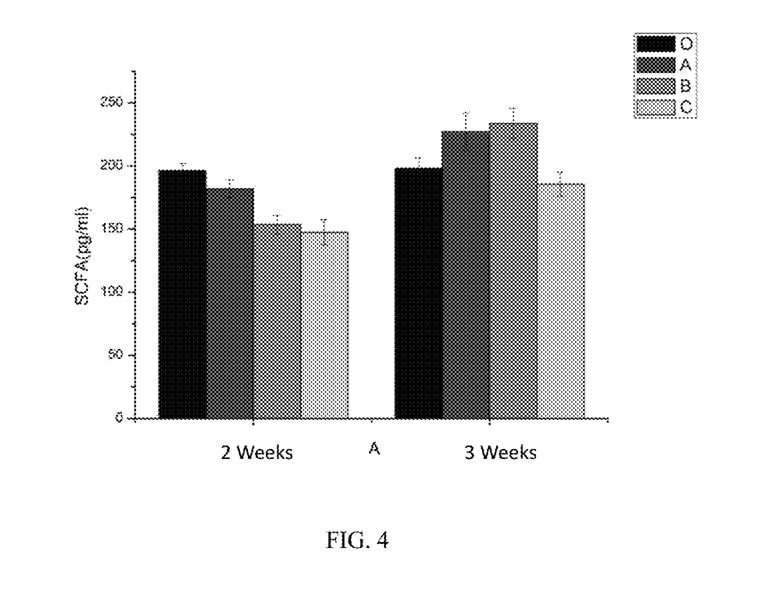
FIG. 4 is a diagram showing changes in the biochemical indicator of short chain fatty acid (SCFA) of mouse serum in an embodiment of the present invention.

It can be seen from Table 1 and FIGS. 2-4, the results of comparing each indicator of the serum of mice in the experimental groups with that in the blank group are as follows.

Experimental group A: the change of the DAO indicator is unstable, the TMAO value has a negative change (increase), and the change of the SCFA is not significant.

Experimental group B: the change of the DAO indicator is not significant, the negative change of the TMAO value at day twenty-one is large (increased), and the change of the SCFA is large.

Experimental group C: the change of the DAO indicator is significant, the change of the TMAO is significant, and the change of the SCFA is significant.

Since diamine oxidase (DAO) is an internal enzyme of intestinal mucosal cells, the level of the DAO in the blood directly expresses the degree of damage of the intestinal mucosa and the level of intestinal permeability. It is generally believed that oligosaccharides selectively promote the proliferation of probiotics in the intestine, thereby improving the health of the host. However, it has also been reported that oligofructose increases the permeability of the rat's intestine, and even increases the ectopic of *Salmonella* at high doses. Excessive consumption of oligosaccharides may also cause intestinal discomfort, such as borborygmus and flatulence. As can be seen from Table 1, at the end of the second week of the experimental period, the mice in the group A have the lowest DAO value, but the DAO value is increased at the end of the third week of the experimental period. The reasons may be that excessive combinations of functional oligosaccharides increase intestinal permeability in mice, resulting in an increase of the DAO value. However, the DAO value of the mice in the group C showed a gradually decreasing process, indicating that the synergistic effect of the formula of the group C made up for the important drawbacks of the formulas of the groups A and B, and the formula of the group C is an ideal formula combination.

Trimethylamine (TMAO), a choline metabolite that depends on intestinal microorganisms, plays an important role in the occurrence and development of cardiovascular diseases. The level of TMAO in the host shows obviously positive correlation with cardiovascular diseases. Intestinal microorganisms use the intake nutrients such as lecithin, choline, and carnitine as sources of carbon energy. Intestinal microorganisms have a trimethylamine lyase (the mammal does not have this enzyme), which can break the C—N bond of these nutrients, and then the trimethylamine is released as a metabolic waste, entered the liver through the portal vein, and is oxidized to form TMAO by the flavin monooxygenase, mainly flavin-containing monooxygenase 3 (FMO3), in the liver.

At the ends of the second week and the third week of the experimental period, the values of the groups A and B were even higher than that of the blank group O, and a negative effect occurred, indicating that although the combination of the functional glycans and the combination of the common glycans have an influence on the intestinal micro-ecology, they have a negative effect on the host at stages. The TMAO value in the serum of the mice in the group C was the lowest, indicating that the feed of the group C can promote the growth of probiotics, balance the microbial steady state, and inhibit the microorganisms that can produce trimethylamine precursors.

Short-chain fatty acids (SCFA) play an important role in maintaining intestinal health in the human body. In particular, butyric acid, as a growth-inducing agent for colonic mucosa and an inhibitor of inflammation, can induce apoptosis of cancer cells and prevent colon cancer. The content of SCFA in the intestine can reflect the bacterial activity and affect the regulation of liver lipids and carbohydrates. The bacteria use oligosaccharides to produce short-chain fatty acids. Referring to FIG. 1, the pH values of the intestinal contents of the mice in the experimental groups A, B, and C were significantly lower than those in the blank group. However, from the analysis of the serum determination results in the second week of the experimental period, it was found that the SCFA in the serum of the mice in the blank group were the highest. At the end of the third week of the experimental period, the serum results showed that the change in the group C was not obvious. This result was related to the decrease of the permeability due to the thickening of the intestinal mucosal, which was consistent with the lowest DAO in the serum of the group C.

In summary, the feeds of the experimental groups A, B, C represent three types of formulas, where the formula of the group C is the most ideal type of formula. The synergistic effect of the components in the group C had a positive effect on the steady state balance of the intestinal micro-ecology and the host without causing side effects. The formulas of the groups A and B had a positive effect on the steady state balance of the intestinal micro-ecology and the host, but they both have certain side effects in some stages. This is further confirmed in the subsequent experimental results.

3.3 Effects on the Villus Height and Fossae of Small Intestine

TABLE 2

Changes of villus height and fossae depth of small intestine after feed intervention in experimental groups

| Treatment | Indicators | | |
|---|---|---|---|
| | villus height (mm) | fossae depth (mm) | V/F |
| O-14 | 0.535 | 0.157 | 3.460 |
| A-14 | 0.494 | 0.133 | 3.791 |
| B-14 | 0.590 | 0.144 | 4.171 |
| C-14 | 0.462 | 0.145 | 3.278 |
| O-21 | 0.272 | 0.075 | 3.833 |
| A-21 | 0.349 | 0.112 | 3.113 |
| B-21 | 0.474 | 0.121 | 4.157 |
| C-21 | 0.584 | 0.130 | 4.757 |

Figure 5:
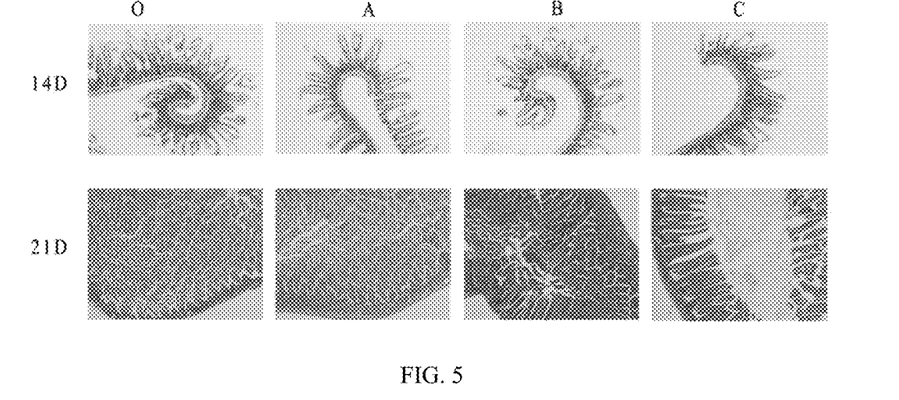
FIG. 5 are diagrams showing changes in height of mouse intestinal villus and fossae section in an embodiment of the present invention.
Figure 6:
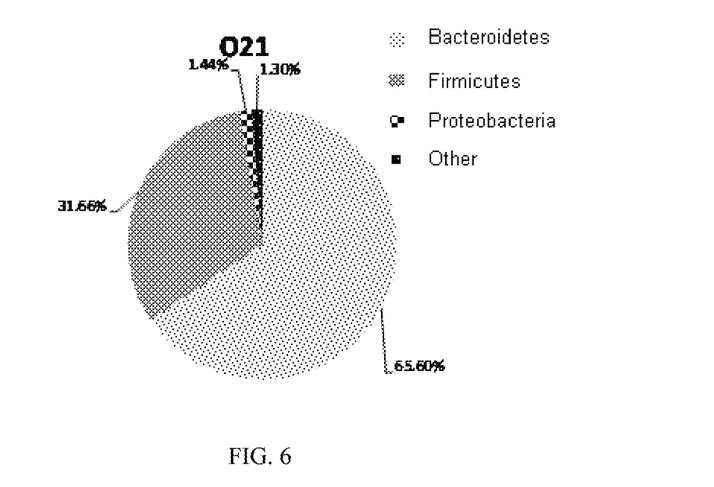
FIG. 6 is a constitution diagram of intestinal flora at a phylum level in mice of a blank group at day twenty-one in an embodiment of the present invention.

Table 2 and FIG. 5 shows changes in the indicators of mice of the experimental groups A, B, C and the blank group O when feeding for 14 days and 21 days. The small intestine is the main part of the nutrient digestion, absorption and transport in the body. Therefore, good intestinal mucosal structure is extremely important for improving the digestive and physiological functions and promoting the growth and development of the body. Small intestine villi, as an important part of the small intestine, not only plays an important role in the absorption of nutrients, but also destroy the colonization of harmful bacteria by the strong swing of the small intestine villi. The effect of probiotics on intestinal morphology and functions may be more than a change in the morphology of the intestinal villi, but also more changes at the cellular level. The ratio of the villus height to the fossae depth reflects the functional state of the small intestine. When the ratio decreases, it indicates that the mucosa is damaged, the digestion and absorption function is decreased and the growth and development of the animal is blocked. After 14 days of feeding, the ratios of the villus height to the fossae depth in the groups A and B were higher than that in the blank group, while the difference between the group C and the blank group was not obvious. After 21 days, the ratios of the villus height to the fossae depth in the group B and the group C were higher than that in the blank group, and the group C performed best. The reasons may be that it promotes the establishment of normal microflora in the gastrointestinal tract of mice, maintains the environmental stability in the digestive tract, and improves the living environment of the intestinal villi. This is further confirmed in the blood biochemical test of the DAO value in the group C.

3.4 Determination of Metabolomics of Intestinal Contents

TABLE 3

Changes of values in some organic acids in experimental groups

| | Compound | Group A | Group B | Group C | Blank group O |
|---|---|---|---|---|---|
| 14D | l-Isoleucine, trimethylsilyl ester | 1351254 | 937933.3 | 1029646 | 6442426 |

TABLE 3-continued

Changes of values in some organic acids in experimental groups

| | Compound | Group A | Group B | Group C | Blank group O |
|---|---|---|---|---|---|
| | L-Leucine, N-(trimethylsilyl)-, trimethylsilyl ester | | 233121.4 | 171788.6 | 1587480 |
| | l-Norvaline, n-propargyloxycarbonyl-, propargyl ester | 206724.3 | 144895.4 | 94160.24 | 143520.8 |
| | L-Tyrosine, N,O-bis(trimethylsilyl)-, trimethylsilyl ester | 445216.2 | 474403.5 | 387425.5 | 1274665 |
| | N,O-Bis-(trimethylsilyl)phenylalanine | 72018.65 | 88755.76 | 75478.61 | 542069.7 |
| | Butanedioic acid, bis(trimethylsilyl) ester | 1.77E+08 | 33792958 | 3.4E+08 | 25217896 |
| | Ethanedioic acid, bis(trimethylsilyl) ester | 1871312 | 3891977 | 3907010 | 4285687 |
| | Pentanoic acid, trimethylsilyl ester | 84519.87 | 346770 | 53365.86 | 2998365 |
| 21D | l-Leucine, trimethylsilyl ester | 260505.9 | 316711.9 | 157854.1 | 566258.5 |
| | L-Norvaline, N-(trimethylsilyl)-, trimethylsilyl ester | 721582.8 | 446013.8 | 703647 | 2844951 |
| | l-Norvaline, n-propargyloxycarbonyl-, propargyl ester | 142513.7 | 83465.25 | 88971.79 | 68541.14 |
| | tyrosine 2 | | | 174611.8 | 222560.6 |
| | N,O-Bis(trimethylsilyl)-L-phenylalanine | 114663.6 | 71594.49 | 39275.48 | 221386.5 |
| | Ethanedioic acid, bis(trimethylsilyl) ester | 4691238 | 4016730 | 5924692 | 4756718 |
| | Butanedioic acid, bis(trimethylsilyl) ester | 10164084 | 31606358 | 242145.9 | 217237.5 |
| | Pentanoic acid, 2-[(trimethylsilyl)oxy]-, trimethylsilyl ester | 166892.4 | 89691.58 | 35602.76 | 55032.92 |

As can be seen from Table 3, when the mice were fed with different feeds, the changes of contents of isoleucine, leucine, valine, tyrosine succinic acid, oxalic acid, valeric acid and isovaleric acid in the intestinal contents of mice are presented. Diabetes cause metabolic disturbance of partial amino acid, having two major characteristics. 1. Total plasma amino acid content and glycogenic amino acid content decrease in diabetes and are significantly negatively correlated with blood glucose. 2. Regardless of the quality of blood glucose control, the content of branched chain amino acids and their proportion in total amino acids are increased.

However, the contents of some amino acids were elevated 5-10 years before the onset of diabetes, especially the levels of five amino acids of isoleucine, leucine, proline, tyrosine and phenylalanine in blood abnormally rose. The experiment clearly shows that the results are more obvious especially after 21 days. The five amino acids have changed significantly with the combination made according to a reasonable feed ratio, which mainly decreased remarkably. It has significant significance for prevention and reduction of the incidence of diabetes.

The evaluation of the indicators related to these amino acids is not only conductive to predicting the risk of diabetes, but also has practical significance for heart disease, tumor (kidney cancer, pancreatic cancer), achieving targeted early intervention and prevention and playing a precise primary prevention role.

Bacteria use oligosaccharides to produce short-chain fatty acids. The increase of the short-chain fatty acid content causes a pH decrease in the intestines. Acetic acid is mainly produced by Bacteroidetes, while butyrate is mainly produced by Firmicutes. Butyric acid is the main source of energy for colon cells, which increases intestinal health, potentially reduces intestinal permeability, and prevents metabolic endotoxemia. When fed for 14 days, compared with the mice of the groups A and B, the mice of the group C showed an increasing content of succinic acid and oxalic acid and a decreasing content of valeric acid; and when fed for 21 days, it was found that the content of oxalic acid increased and the contents of succinic acid and isovaleric acid decreased.

3.5 Determination of 16S DNA of Intestinal Contents

In this experiment, four phylums of bacteria were detected in the intestinal contents of mice, wherein Bacteroidetes, Firmicutes and Proteobacteria were the three most abundant phylums. FIGS. 6-9 showed a composition of intestinal flora in phylum of mice on day twenty-one, indicating that in the mice of the blank group O, the abundance of Bacteroidetes reached 65.6%, Firmicutes reached 31.66%, and Proteobacteria reached 1.44%.

Figure 7:
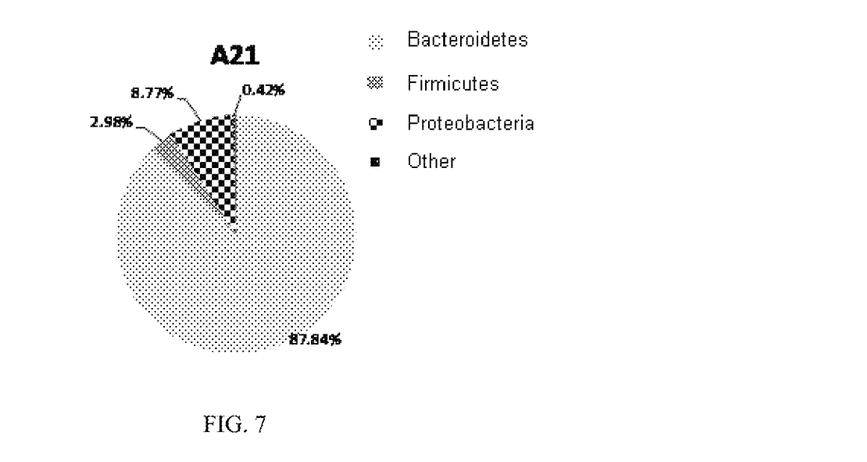
FIG. 7 is a constitution diagram of intestinal flora at a phylum level in mice of the experimental group A at day twenty-one in an embodiment of the present invention.

In the mice of the experimental group A, the abundances of the three phylums reached 87.84%, 2.98%, and 8.77%, respectively.

Figure 8:
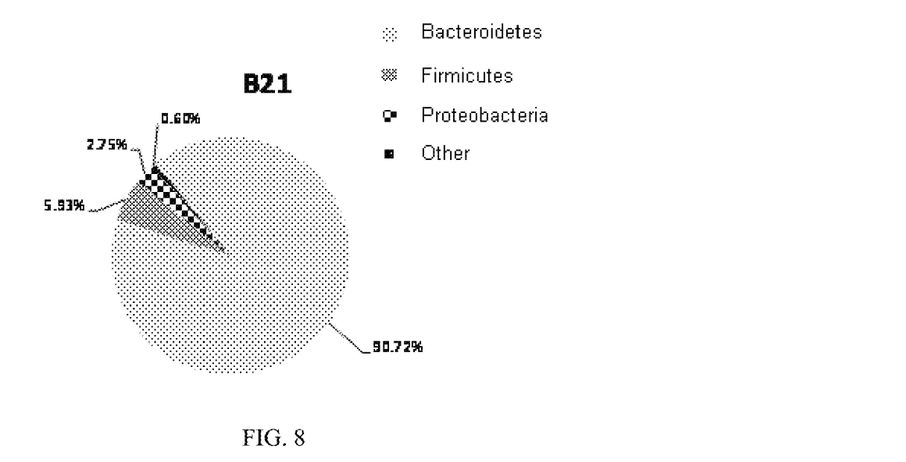
FIG. 8 is a constitution diagram of intestinal flora at a phylum level in mice of the experimental group B at day twenty-one in an embodiment of the present invention.

In the mice of the experimental group B, the abundances of the three phylums reached 90.72%, 5.93%, 2.75%.

Figure 9:
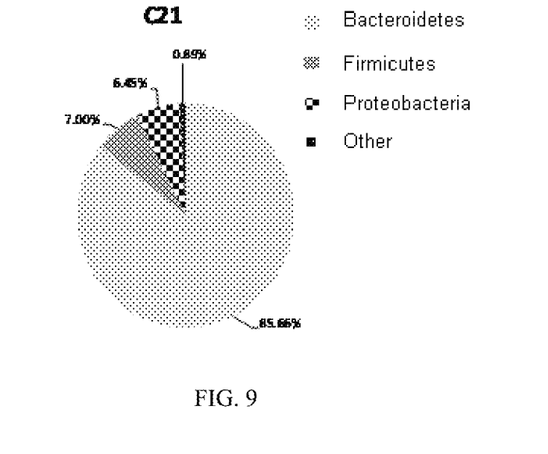
FIG. 9 is a constitution diagram of intestinal flora at a phylum level in mice of the experimental group C at day twenty-one in an embodiment of the present invention.

In the mice of the experimental group C, the abundances of the three phylums reached 85.65%, 7.00%, and 6.45%, respectively.

Compared with the blank group, it showed that in the experimental groups A, B and C, the abundances of Bacteroidetes and Proteobacteria increased, and the abundance of Firmicutes decreased. It can be seen that the proliferation of the Bacteroidetes and Proteobacteria are promoted by the ingestion of oligosaccharides in mice, and the growth of the Firmicutes is inhibited.

Figure 10:
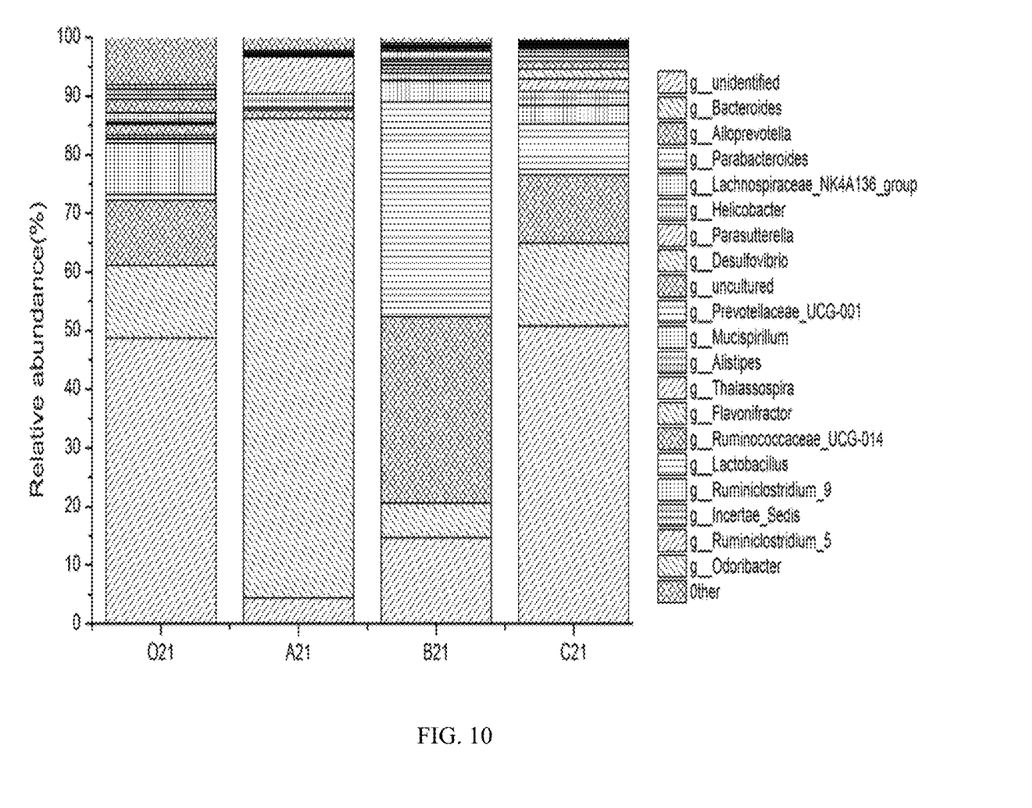
FIG. 10 is a constitution diagram of intestinal flora at a genus level in mice of four experimental groups at day twenty-one in an embodiment of the present invention.

In this experiment, 14 genera of bacteria having a proportion of more than 0.1% were detected in the intestinal contents of the mice. Bacteroides, Alloprevotella, Prebacteriodes, Lachnospiraceae, and Parasutterella were the major genera of the intestinal contents. FIG. 10 showed a composition of intestinal flora in genus of the mice on the day twenty-one, indicating the following.

After the mice ingested the feed of the experimental group A, the Bacteroides in the intestinal contents increased significantly, while the Bacteroides in the intestinal contents of the mice in the group B were significantly decreased, and the changes in Bacteroides in the group C were not obvious, indicating that the combination of the functional oligosaccharides has the effect of promoting the proliferation of Bacteroides, while the common oligosaccharides have no such effect.

In the intestinal contents of the mice in the groups B and C, Alloprevotella and Parabacteriodes increased, while decreased in the group A, indicating that the common oligosaccharides have the function to promote the proliferation of Alloprevotella and Parabacteriodes.

Compared with the blank group, in the samples of the groups A, B, and C, Lachnospiraceae decreased, while Parasutterella increased. Galactooligosaccharides and inulin, as prebiotics, are not digested and absorbed by the body but directly enter the large intestine, playing an important role in regulating intestinal flora, maintaining normal environment in the intestine, regulating intestinal function, and improving the health of the body. Polydextrose, as a water-soluble dietary fiber, can shorten the emptying time of food in the stomach and effectively improve intestinal function. After being ingested into the human body, the polydextrose is fermented only in the lower half part of the gastrointestinal tract to produce short-chain fatty acids such as butyric acid, which lowers the pH in the intestine, and helps fight infection. The insoluble dietary fiber extracted from wheat bran cannot be dissolved in water and cannot be fermented by microorganisms in the large intestine, and can merely reduce the residence time of excreta in the intestine, increase the volume of intestinal contents, and play a role in improving the microbial reproductive environment and loosening bowel to relieve constipation.

This experiment focuses on verifying a synergistic effect of combinations of functional glycans and common glycans. The synergistic effect mainly includes the following two aspects. First, changes of suitable microbial abundance and the microbial living environment. Second, effects of balanced microbial nutrition on changes of physiological indicators of the host. The experimental results show that all types of glycan combinations have significant effects on mouse intestinal micro-ecology and physiological indicators. Among them, the synergistic effect of the combination containing the functional glycans and the common glycans improves the steady state of the host intestinal microbe, and has a positive effect on the host without causing side effects. Single addition of the combination of functional glycans or the combination of common glycans in the experimental groups have a positive effect on the host and also cause certain side effects in stages.

3.6 Experimental Conclusions and Analysis:

In this experiment, the effects of different types of glycan combinations on the intestinal micro-ecological system of mice were investigated. Four feed formulations, including groups O, A, B and C, were used to feed the mice. The analysis of intestinal contents in the mice by macrogenome showed that different dietary diets have great effects on the intestinal flora. The combination of galactooligosaccharide and inulin (group A) caused a significant increase in Bacteroides, a significant decrease in Prevotella, and a decrease in the diversity of the intestinal flora. Although bifidobacteria increased significantly, the proportion thereof was relatively small. In the mice fed with the combination of polydextrose and insoluble dietary fiber (group B), Bacteroides significantly decreased, and Prevotella and Bacteroides thetaiotaomicron significantly increased. In the mice fed with the combination of galactooligosaccharide, inulin, polydextrose and insoluble cellulose composite (group C), the genera such as Bacteroides, Prevotella had fluctuations, but the changes were not significant, indicating that different dietary diets had a great effect on the intestinal flora. Further, the data of the pH of the colon contents and the SCFA in the blood indicated that the oligosaccharides and dietary fibers were fermented to produce a large amount of short-chain fatty acids, causing the pH to decrease. The data analysis of the DAO and TMAO contents in the serum and the intestinal villi showed that the mice in the group C performed best, indicating that the diversity of glycans and dietary fiber contributed to the health of the intestinal micro-ecological system in normal mice.

In summary, various types of glycan combinations have significant effects on mouse intestinal micro-ecology and physiological indicators in mice. Among them, the synergistic effect of the combination of functional glycans and the combination of common glycans improves the steady state of host intestinal microbe and has a positive effect on the host without causing side effects. The experiment group where the combination of functional glycans or the combination of common glycans are individually added have a positive effect on the host and also causes certain side effects in stages. It shows that simply adding nutritional enhancers and supplements such as functional glycans, common glycans and the like cannot reach a balanced diet. However, the balanced nutrition of the formula combination containing functional glycans and common glycans is the key to maintain the intestinal micro-ecological at a steady state and to protect human health.

The combination for improving intestinal micro-ecology of the present invention includes functional glycans and common glycan dietary fiber composites. A plurality of the glycans have a remarkable synergistic effect, which generates positive effects on the host without negative effects. A combined nutrients and an intestinal environment that is beneficial to the proliferation are provided for beneficial bacteria and neutral bacteria in the intestine, which enriches the metabolites of intestinal flora including primary metabolites and secondary metabolites beneficial to the human body, improves the intestinal micro-ecology, and achieves the effect of preventing chronic diseases targeted by improving intestinal microbial steady state. The balanced nutritious food of the present invention further provides a balanced nutrition for the intestinal flora and the human body (super organism), and provides a combination for maintaining the steady state balance of the intestinal micro-ecology with its suitable staple food as a carrier, which effectively improves the human body in a sub-health state, and prevents chronic diseases that cause major human health problems.

The above description shows only preferred embodiments of the present invention and is not intended to limit the present invention in any way. Some simple improvements, equivalent changes or modifications using the technical content disclosed above by those skilled in the art should all fall within the scope of the present invention.

What is claimed is:

1. A combination for improving intestinal micro-ecology and preventing chronic diseases, comprising:
   an inulin,
   a galactooligosaccharide,
   a polydextrose,
   an insoluble dietary fiber, and
   at least one enhancer comprising at least one of xylooligosaccharide, L-arabinose, stachyose, guar gum, wherein a ratio of the inulin, the galactooligosaccharide, the polydextrose and the insoluble dietary fiber in a formula is 3.5:4:3.5:4.

2. The combination for improving the intestinal micro-ecology and preventing the chronic diseases according to claim 1, wherein, the inulin is oligofructose, polyfructose, or a mixture of the oligofructose and the polyfructose.

3. A composite nutritious food comprising the combination according to claim 1, further comprising a cereal flour, wherein a ratio of the cereal flour to the combination in the composite nutritious food is (50-95):(5-50) by weight.

4. The composite nutritious food according to claim 3, wherein, the ratio of the cereal flour to the combination in the composite nutritious food is (70-95):(5-30) by weight.

5. The composite nutritious food according to claim 3, wherein, the cereal flour is one or more selected from the group consisting of a wheat flour, a rice flour, a corn flour and a whole potato powder; and the composite nutritious food is in a form of compound rice, flour, noodles, pasta, rice noodles, bread, bread dough or bread mix.

6. The composite nutritious food according to claim 5, wherein, a method for preparing the compound rice comprises mixing the cereal flour with the combination, and extruding into a shape of rice by an extruding process.

7. A method for preventing inflammatory bowel disease, comprising the step of administering to a patient in need thereof a food or a medicament comprising the combination of claim 1.

8. A method for improving gastrointestinal motility and preventing constipation, comprising the step of administering to a patient in need thereof a food or a medicament comprising the combination of claim 1.

9. A method for preventing diabetes, comprising the step of administering to a patient in need thereof a food or a medicament comprising the combination of claim 1.

10. A method for preventing cardiovascular and cerebrovascular diseases, comprising the step of administering to a patient in need thereof a food or a medicament comprising the combination of claim 1.

11. A method for regulating intestinal flora to enhance an immune ability, comprising the step of administering to a patient in need thereof a food or a medicament comprising the combination of claim 1.

12. The composite nutritious food according to claim 3, wherein, the inulin is oligofructose, polyfructose, or a mixture of the oligofructose and the polyfructose.

13. The method according to 7, wherein, the inulin is oligofructose, polyfructose, or a mixture of the oligofructose and the polyfructose.

14. The method according to 8, wherein, the inulin is oligofructose, polyfructose, or a mixture of the oligofructose and the polyfructose.

15. The method according to 9, wherein, the inulin is oligofructose, polyfructose, or a mixture of the oligofructose and the polyfructose.

16. The method according to 10, wherein, the inulin is oligofructose, polyfructose, or a mixture of the oligofructose and the polyfructose.

17. The method according to 11, wherein, the inulin is oligofructose, polyfructose, or a mixture of the oligofructose and the polyfructose.

* * * * *